(12) United States Patent　　　(10) Patent No.:　US 12,594,167 B2
Bader et al.　　　　　　　　　　(45) Date of Patent:　　　Apr. 7, 2026

(54) HIP IMPLANT SYSTEM

(71) Applicants:Aesculap AG, Tuttlingen (DE); IHI Ionbond AG, Zurich (CH)

(72) Inventors: Christian Bader, Huefingen (DE); Janine Fechter, Haigerloch (DE); Jens Schneider, Radolfzell (DE)

(73) Assignees: Aesculap AG, Tuttlingen (DE); IHI Ionbond AG, Zurich (CH)

( * ) Notice: Subject to any disclaimer, the term of this patent is extended or adjusted under 35 U.S.C. 154(b) by 671 days.

(21) Appl. No.: 17/927,972

(22) PCT Filed: May 28, 2021

(86) PCT No.: PCT/EP2021/064374

§ 371 (c)(1),
(2) Date: Nov. 28, 2022

(87) PCT Pub. No.: WO2021/244972

PCT Pub. Date: Dec. 9, 2021

(65) Prior Publication Data

US 2023/0210668 A1　　Jul. 6, 2023

(30) Foreign Application Priority Data

Jun. 3, 2020　(DE) ..................... 10 2020 206 954.9

(51) Int. Cl.
A61F 2/34　　　　　(2006.01)
A61F 2/30　　　　　(2006.01)
(52) U.S. Cl.
CPC ........... *A61F 2/34* (2013.01); *A61F 2/30767* (2013.01); *A61F 2002/30929* (2013.01);
(Continued)

(58) Field of Classification Search
CPC .............. A61F 2/34; A61F 2310/00892; A61F 2310/00754; A61F 2310/00886; A61F 2002/30929; A61F 2002/3208
See application file for complete search history.

(56) References Cited

U.S. PATENT DOCUMENTS 5,108,447 A　　4/1992　Zeiler et al.
2009/0005879 A1 *　1/2009　Tuke ........................ A61F 2/34
　　　　　　　　　　　　　　　　　　　　623/22.24
(Continued)

FOREIGN PATENT DOCUMENTS

DE　　2811603 A1　9/1979
EP　　0445068 A1　9/1991
(Continued)

OTHER PUBLICATIONS

Search Report received in International Application No. PCT/EP2021/064374 dated Aug. 30, 2021, with translation, 5 pages.
(Continued)

*Primary Examiner* — Jerrah Edwards
*Assistant Examiner* — Teresa M Dudden
(74) *Attorney, Agent, or Firm* — Christopher A. Rothe; CM Law

(57)　　　　　ABSTRACT

A hip implant system includes an artificial acetabular cup and an artificial acetabular liner. The liner includes or consists of a metal or an alloy, and is coated at least in sections with a ceramic coating.

15 Claims, 3 Drawing Sheets

(52) U.S. Cl.
CPC ... *A61F 2/3094* (2013.01); *A61F 2002/30971* (2013.01); *A61F 2002/348* (2013.01); *A61F 2310/00592* (2013.01); *A61F 2310/00754* (2013.01); *A61F 2310/00886* (2013.01); *A61F 2310/00892* (2013.01)

(56) References Cited

U.S. PATENT DOCUMENTS

| | | | | |
|---|---|---|---|---|
| 2009/0187255 A1* | 7/2009 | Jani | .......................... | C22C 29/00 623/23.56 |
| 2009/0210068 A1* | 8/2009 | Zeller | ................... | C23C 28/347 623/18.11 |

FOREIGN PATENT DOCUMENTS

| | | | |
|---|---|---|---|
| JP | 2010500139 | A | 1/2010 |
| JP | 2013226444 | A | 11/2013 |
| WO | 2007121242 | A2 | 10/2007 |
| WO | 2008019923 | A2 | 2/2008 |
| WO | 2011141169 | A1 | 11/2011 |

OTHER PUBLICATIONS

Office Action received in Japanese Application No. 2022-574631 dated Jul. 15, 2025, with translation, 4 pages.

* cited by examiner

HIP IMPLANT SYSTEM

CROSS-REFERENCE TO RELATED APPLICATIONS

This application is the United States national stage entry of International Application No. PCT/EP2021/064374, filed May 28, 2021, and claims priority to German Application No. 10 2020 206 954.9, filed Jun. 3, 2020. The contents of International Application No. PCT/EP2021/064374 and German Application No. 10 2020 206 954.9 are incorporated by reference herein in their entireties.

FIELD

The invention relates to a hip implant system.

BACKGROUND

Hip implant systems are nowadays used routinely to replace damaged or worn hip joints. Besides an artificial acetabular cup, corresponding hip implant systems usually comprise an artificial acetabular liner, for example made of a plastic, a ceramic or a metal alloy, which can be inserted directly into the artificial acetabular cup. Metallic acetabular liners often consist of a metal alloy containing cobalt and/or chromium. An artificial femoral liner which can be inserted directly into the artificial acetabular liner, and optionally an artificial articular head, with or without an artificial femoral stem, which can be inserted into the femoral liner, may additionally be provided.

After the implantation of a hip implant system, micro-movements may often take place between the artificial acetabular cup and the artificial acetabular liner because of dynamic loads. It is a problem that these micro-movements may cause frictional corrosion, that is to say so-called fretting, so that in the case of an artificial acetabular liner made of a metal alloy containing cobalt and/or chromium, cobalt ions and/or chromium ions may be released into surrounding patient tissue. Furthermore, cobalt ions and/or chromium ions may generally be released by wear of the acetabular liner. The in vivo release of cobalt ions and/or chromium ions may in turn lead to allergic and/or toxic tissue reactions, so that the risk of a surgical revision operation increases.

SUMMARY

The object of the invention is to provide a hip implant system which partially or fully avoids the disadvantages described in the introduction in connection with hip implant systems of the generic type, and which in particular reduces or even entirely prevents an in vivo release of cobalt ions and/or chromium ions.

The invention relates to a hip implant system.

The hip implant system comprises an artificial acetabular cup and an artificial acetabular liner. The artificial acetabular liner comprises a metal or an alloy, preferably an alloy containing cobalt and/or chromium, or consists of a metal or an alloy, preferably an alloy containing cobalt and/or chromium. Expediently, the artificial acetabular liner can be inserted into the artificial acetabular cup.

The hip implant system according to the present invention is distinguished particularly in that the artificial acetabular liner is coated at least in sections, in particular only in sections, or fully with a ceramic coating.

The term "hip implant system" is intended in the context of the present invention to mean a set of individual components, wherein the components, in particular during a surgical intervention, can be assembled or joined, in particular modularly, to form a hip implant for replacement or partial replacement of a natural hip joint. The set comprises as components at least one artificial acetabular cup according to the invention and an artificial acetabular liner according to the invention. The set may additionally comprise further components, in particular as described in more detail below.

The term "ceramic coating" is intended in the context of the present invention to mean a coating which comprises a ceramic, in particular a hard ceramic, or consists of a ceramic, in particular a hard ceramic.

The invention is based, in particular, on the surprising discovery that in vivo release of metal ions that are detrimental to health, in particular cobalt ions and/or chromium ions, at contiguous surfaces of modularly joined hip implant components may be (significantly) reduced or even entirely avoided by an at least in sections coating with a ceramic material.

In this way, the risk of postsurgical complications, particularly in the form of allergic or toxic reactions, and therefore the risk of surgical reinterventions, can be reduced or even entirely eliminated.

Preferably, the artificial acetabular cup comprises an at least in sections, in particular only in sections, or fully concavely configured reception region for receiving the artificial acetabular liner. The at least in sections concavely configured reception region preferably comprises an at least in sections, in particular only in sections, or fully concave inner face of the artificial acetabular cup. Particularly preferably, the at least in sections concavely configured reception region is defined or formed by the at least in sections concave inner face and by a circumferential edge, bounding the at least in sections concave inner face, of the artificial acetabular cup.

Particularly preferably, the artificial acetabular cup is at least in sections, in particular only in sections, or fully configured in the form of a shell segment, particularly in the form of a spherical shell segment. Preferably, the artificial acetabular cup comprises an at least in sections, in particular only in sections, or fully convex outer face and an at least in sections, in particular only in sections, or fully concave inner face, which are respectively bounded by a circumferential edge of the artificial acetabular cup.

Alternatively, the artificial acetabular cup preferably comprises an at least in sections, in particular only in sections, or fully conically or frustoconically configured reception region for receiving the artificial acetabular liner. The at least in sections conically or frustoconically configured reception region preferably comprises an at least in sections, in particular only in sections, or fully conical or frustoconical inner face of the artificial acetabular cup. Particularly preferably, the at least in sections conically or frustoconically configured reception region is defined or formed by the at least in sections conical or frustoconical inner face and by a circumferential edge, bounding the at least in sections conical or frustoconical inner face, of the artificial acetabular cup. Preferably, the artificial acetabular cup comprises an at least in sections, in particular only in sections, or fully conical or frustoconical outer face and an at least in sections, in particular only in sections, or fully conical or frustoconical inner face, which are respectively bounded by a circumferential edge of the artificial acetabular cup.

The artificial acetabular cup preferably comprises a bio-compatible metal, or preferably consists of such a metal. The metal may, in particular, be titanium. It may furthermore be preferred for the artificial acetabular cup to be coated on an outer face, in particular on one of the outer faces mentioned in the preceding paragraphs, at least in sections, in particular only in sections, or fully with a porous coating comprising or consisting of titanium and/or a titanium alloy and/or hydroxyapatite. In this way, improved osseointegration and in particular secondary stability of the artificial acetabular cup may advantageously be achieved. Alternatively or in combination, the outer face of the artificial acetabular cup may be configured with a macrostructure, for example with tooth-like projections. By a correspondingly configured acetabular cup, high clamping and frictional forces may particularly advantageously be produced in vivo, so that sufficient primary stability of the artificial acetabular cup can be ensured.

Preferably, the artificial acetabular liner comprises an at least in sections, in particular only in sections, or fully concavely configured reception region for receiving an artificial femoral liner. The at least in sections concavely configured reception region preferably comprises an at least in sections, in particular only in sections, or fully concave inner face/articular or glide face of the artificial acetabular liner. Particularly preferably, the at least in sections concavely configured reception region is defined or formed by the at least in sections concave inner face/articular or glide face and by a circumferential edge, bounding the at least in sections concave inner face/articular or glide face, of the artificial acetabular liner.

Particularly preferably, the artificial acetabular liner is at least in sections, in particular only in sections, or fully configured in the form of a shell segment, particularly in the form of a spherical shell segment. Preferably, the artificial acetabular liner comprises an at least in sections, in particular only in sections, or fully convex outer face and an at least in sections, in particular only in sections, or fully concave inner face/articular or glide face, which are respectively bounded by a circumferential edge of the artificial acetabular liner.

Particularly preferably, the artificial acetabular liner has a convex outer shape complementary to the concavely configured reception region of the artificial acetabular cup.

Alternatively, the artificial acetabular liner preferably comprises an at least in sections, in particular only in sections, or fully conically or frustoconically configured reception region for receiving an artificial femoral liner. The at least in sections conically or frustoconically configured reception region preferably comprises an at least in sections, in particular only in sections, or fully conical or frustoconical inner face/articular or glide face of the artificial acetabular liner. Particularly preferably, the at least in sections conically or frustoconically configured reception region is defined or formed by the at least in sections conical or frustoconical inner face/articular or glide face and by a circumferential edge, bounding the at least in sections concave inner face/articular or glide face, of the artificial acetabular liner. Preferably, the artificial acetabular liner comprises an at least in sections, in particular only in sections, or fully conical or frustoconical outer face and an at least in sections, in particular only in sections, or fully conical or frustoconical inner face/articular or glide face, which are respectively bounded by a circumferential edge of the artificial acetabular liner. Preferably, the artificial acetabular liner has a conical or frustoconical outer shape complementary to the conically or frustoconically configured reception region of the artificial acetabular cup.

In a further embodiment of the invention, only an outer face, in particular only a convex, conical or frustoconical outer face, of the artificial acetabular liner is coated at least in sections, in particular only in sections, or fully with the ceramic coating.

In a further embodiment of the invention, only an inner face, in particular only a concave, conical or frustoconical inner face, of the artificial acetabular liner is coated at least in sections, in particular only in sections, or fully with the ceramic coating.

In a further embodiment of the invention, the artificial acetabular liner is coated fully with the ceramic coating.

In a further embodiment of the invention, the ceramic coating is constructed in a plurality of layers. In other words, in a further embodiment of the invention the ceramic coating is formed as a multilayer layer system.

In a further embodiment of the invention, the ceramic coating comprises at least one non-oxide ceramic or the ceramic coating consists at least of a non-oxide ceramic. The at least one non-oxide ceramic is preferably selected from the group consisting of chromium nitride (CrN), chromium carbonitride (CrCN), chromium zirconium nitride (CrZrN) and zirconium nitride (ZrN). Preferably, the ceramic coating comprises, in particular exclusively, chromium nitride and chromium carbonitride. More preferably, the ceramic coating comprises, in particular exclusively, chromium nitride, chromium carbonitride and zirconium nitride. In particular, the ceramic coating may be free of chromium zirconium nitride. Particularly preferably, the ceramic coating comprises, in particular exclusively, chromium nitride, chromium carbonitride, chromium zirconium nitride and zirconium nitride.

The ceramic coating preferably comprises at least one chromium nitride layer (CrN layer), in particular (only) one chromium nitride layer, two chromium nitride layers or three chromium nitride layers. Alternatively or in combination, the ceramic coating preferably comprises at least one chromium carbonitride layer (CrCN layer), in particular (only) one chromium carbonitride layer or two chromium carbonitride layers. Alternatively or in combination, the ceramic coating preferably comprises at least one chromium zirconium nitride layer (CrZrN layer), in particular (only) one chromium zirconium nitride layer. Alternatively or in combination, the ceramic coating preferably comprises at least one zirconium nitride layer (ZrN layer), in particular (only) one zirconium nitride layer. In particular, the ceramic coating may consist of one or more of the aforementioned layers or of all the aforementioned layers.

The term "chromium nitride layer" is intended in the context of the present invention to mean a layer which comprises chromium nitride, in particular as the main constituent, or consists of chromium nitride.

The term "chromium carbonitride layer" is intended in the context of the present invention to mean a layer which comprises chromium carbonitride, in particular as the main constituent, or consists of chromium carbonitride.

The term "chromium zirconium nitride layer" is intended in the context of the present invention to mean a layer which comprises chromium zirconium nitride, in particular as the main constituent, or consists of chromium zirconium nitride.

The term "zirconium nitride layer" is intended in the context of the present invention to mean a layer which comprises zirconium nitride, in particular as the main constituent, or consists of zirconium nitride.

Further preferably, the ceramic coating may comprise an alternating sequence of (the) chromium nitride layers and chromium carbonitride layers.

In a further embodiment of the invention, the ceramic coating comprises at least one chromium nitride layer (CrN layer), in particular (only) one chromium nitride layer, two chromium nitride layers or three chromium nitride layers, at least one chromium carbonitride layer (CrCN layer), in particular (only) one chromium carbonitride layer or two chromium carbonitride layers, at least one chromium zirconium nitride layer (CrZrN layer), in particular (only) one chromium zirconium nitride layer, and at least one zirconium nitride layer (ZrN layer), in particular (only) one zirconium nitride layer. In particular, the ceramic coating may consist of the aforementioned layers.

Alternatively, the ceramic coating may comprise at least one chromium nitride layer, in particular (only) one chromium nitride layer, two chromium nitride layers or three chromium nitride layers, at least one chromium carbonitride layer, in particular (only) one chromium carbonitride layer or two chromium carbonitride layers, and at least one zirconium nitride layer, in particular (only) one zirconium nitride layer. In particular, the ceramic coating may consist of the aforementioned layers.

In a further embodiment of the invention, the ceramic coating comprises three chromium nitride layers, two chromium carbonitride layers, one, i.e. only one, chromium zirconium nitride layer and one, i.e. only one, zirconium nitride layer. Preferably, the chromium nitride layers and the chromium carbonitride layers are arranged in an alternating sequence above one another. In particular, the ceramic coating may consist of the aforementioned layers.

Alternatively, the ceramic coating may comprise three chromium nitride layers, two chromium carbonitride layers and one, i.e. only one, zirconium nitride layer. Preferably, the chromium nitride layers and the chromium carbonitride layers are arranged in an alternating sequence above one another. In particular, the ceramic coating may consist of the aforementioned layers.

In a further embodiment of the invention, the ceramic coating is formed as a multilevel or multilayer layer system in which a first chromium nitride layer is, preferably directly, covered by or coated with a first chromium carbonitride layer, the first chromium carbonitride layer is, preferably directly, covered by or coated with a second chromium nitride layer, the second chromium nitride layer is, preferably directly, covered by or coated with a second chromium carbonitride layer, the second chromium carbonitride layer is, preferably directly, covered by or coated with a third chromium nitride layer, the third chromium nitride layer is, preferably directly, covered by or coated with a chromium zirconium nitride layer and the chromium zirconium nitride layer is, preferably directly, covered by or coated with a zirconium nitride layer. Preferably, the first chromium nitride layer is formed directly on a surface, in particular a convex, conical or frustoconical outer face/glide face, and/or a concave, conical or frustoconical inner face/glide face, of the artificial acetabular liner.

Alternatively, the ceramic coating may be formed as a multilevel or multilayer layer system in which a first chromium nitride layer is, preferably directly, covered by or coated with a first chromium carbonitride layer, the first chromium carbonitride layer is, preferably directly, covered by or coated with a second chromium nitride layer, the second chromium nitride layer is, preferably directly, covered by or coated with a second chromium carbonitride layer, the second chromium carbonitride layer is, preferably directly, covered by or coated with a third chromium nitride layer and the third chromium nitride layer is, preferably directly, covered by or coated with a zirconium nitride layer. Preferably, the first chromium nitride layer is formed directly on a surface, in particular a convex, conical or frustoconical outer face/glide face, and/or a concave, conical or frustoconical inner face/glide face, of the artificial acetabular liner.

In a further embodiment of the invention, the zirconium nitride layer forms an outer closure or cover layer of the ceramic coating. Preferably, the closure or cover layer is formed directly, i.e. immediately, on a chromium nitride layer, chromium carbonitride layer or chromium zirconium nitride layer.

The advantages of the present invention are particularly strongly pronounced with the non-oxide ceramic coating described in the preceding paragraphs. It is furthermore advantageous that the non-oxide ceramic coating described in the preceding paragraphs exhibits a high abrasion strength and therefore particularly good adhesion especially in the case of an artificial acetabular liner made of an alloy containing cobalt and/or chromium.

Alternatively, the ceramic coating may comprise at least one oxide ceramic or consist of at least one oxide ceramic. The at least one oxide ceramic is preferably selected from the group consisting of aluminum oxide ($Al_2O_3$), zirconium dioxide ($ZrO_2$), titanium dioxide ($TiO_2$) and chromium(III) oxide ($Cr_2O_3$). The aforementioned aluminum oxide is preferably aluminum oxide of the corundum type. The aforementioned zirconium dioxide is preferably zirconium dioxide of the baddeleyite type. The aforementioned titanium dioxide is preferably titanium dioxide of the rutile type. The aforementioned chromium(III) oxide is preferably chromium(III) oxide of the corundum type.

The ceramic coatings described in the preceding paragraphs may, for example, be applied onto the artificial acetabular liner by physical vapor deposition (PVD).

In a further embodiment of the invention, the ceramic coating, in particular one of the chromium nitride layers, in particular the first chromium nitride layer, is formed directly, i.e. immediately, on the artificial acetabular liner, i.e. on a surface, in particular a convex, conical or frustoconical outer face, and/or a concave, conical or frustoconical inner face/articular or glide face, of the artificial acetabular liner.

Alternatively, an intermediate layer, in particular made of a metal, an alloy or a ceramic, may be formed between the ceramic coating and the artificial acetabular liner, i.e. between the ceramic coating and a surface, in particular a convex, conical or frustoconical outer face/glide face, and/or a concave, conical or frustoconical inner face/glide face, of the artificial acetabular liner. The metal may, for example, be niobium, tantalum or zirconium. The alloy may, for example, be a zirconium alloy or niobium alloy. The ceramic may, for example, be a ceramic which contains zirconium, particularly in elemental and/or metallic form.

In a further embodiment of the invention, the ceramic coating has a thickness of from 0.5 µm to 10 µm, in particular from 1.5 µm to 7 µm, preferably from 2.5 µm to 5 µm, particularly preferably from 3 µm to 4 µm. Particularly by the coating thicknesses disclosed in this paragraph, the release barrier in vivo for cobalt ions and/or chromium ions may additionally be increased without there being a (significant) risk that the ceramic coating separates from the artificial acetabular liner because of its layer thickness.

In a further embodiment of the invention, an inner face, in particular a concave, conical or frustoconical inner face, of the artificial acetabular liner, in particular as described in the preceding paragraphs, has a surface roughness Ra (mean roughness value measured according to DIN EN ISO 4287) of ≤0.5 μm, preferably ≤0.05 μm, and/or an outer face, in particular a concave, conical or frustoconical outer face, of the artificial acetabular liner, in particular as described in the preceding paragraphs, has a surface roughness Ra (mean roughness value measured according to DIN EN ISO 4287) of ≤1 μm, preferably ≤0.6 μm. Particularly by the surface roughnesses disclosed in this paragraph, interlocking of surfaces of the artificial acetabular liner and of the artificial acetabular cup and/or interlocking of surfaces of the artificial acetabular liner and of an artificial femoral liner may be achieved particularly advantageously. Furthermore, in particular the surface roughnesses disclosed in this paragraph have the advantage that they reduce the risk of separation of the ceramic coating from the artificial acetabular liner and moreover—in the event of micro-movements of the artificial acetabular liner and/or of the artificial acetabular cup and/or of the artificial femoral liner—cause less wear.

In a further embodiment of the invention, particularly in the uncoated state, i.e. without the ceramic coating, the artificial acetabular liner has a thickness, in particular wall thickness, of from 2 mm to 3 mm. The thicknesses, in particular wall thicknesses, disclosed in this paragraph have the advantage that they allow a flexible, in particular resilient, configuration of the artificial acetabular liner. Moreover, after joining of the artificial acetabular liner into the artificial acetabular cup, they advantageously allow higher contact stresses so that the risk of micro-movements of the artificial acetabular liner and/or of the artificial acetabular cup and therefore the risk of frictional corrosion may additionally be reduced.

In a further configuration of the invention, the artificial acetabular liner has a cone angle θ of from 15° to 25°, in particular from 16° to 21°. The term "cone angle" is in this case intended to mean the angle between a symmetry axis (central axis) and a conical outer face of the acetabular liner. Particularly by the cone angles disclosed in this paragraph, high clamping forces may be produced between the artificial acetabular liner and the artificial acetabular cup, so that the risk of relative movements between the artificial acetabular liner and the artificial acetabular cup and therefore the risk of undesired metal ion release, in particular cobalt ion and/or chromium ion release, may likewise be reduced.

In a further embodiment of the invention, the artificial acetabular liner and the artificial acetabular cup in an assembled or joined state are connected to one another with a force fit or friction fit. Preferably, the artificial acetabular liner and the artificial acetabular cup in an assembled or joined state are clamped to one another, preferably conically clamped to one another. Particularly preferably, the artificial acetabular liner and the artificial acetabular cup in an assembled or joined state are clamped to one another by means of a conical or frustoconical outer face of the artificial acetabular liner and a conical or frustoconical inner face, complementary thereto, of the artificial acetabular cup.

In a further embodiment of the invention, the alloy is an alloy containing cobalt and/or chromium, in particular a cobalt-chromium-molybdenum alloy. The cobalt-chromium-molybdenum alloy may have a cobalt mass fraction of from 62% to 66%, a chromium mass fraction of from 27% to 31% and a molybdenum mass fraction of from 4% to 5%. The cobalt-chromium-molybdenum alloy may furthermore comprise carbon and/or silicon and/or manganese and/or iron, particularly in small amounts and/or in the form of impurities.

In a further embodiment of the invention, the hip implant system furthermore comprises an artificial femoral liner. The artificial femoral liner can expediently be inserted into the artificial acetabular liner. The artificial acetabular liner and the artificial femoral liner preferably form a ball-and-socket joint in a joined or mounted state, in particular after the artificial acetabular liner has been inserted into the artificial femoral liner.

The artificial femoral liner preferably comprises an at least in sections, in particular only in sections, or fully concavely configured reception region for receiving an artificial femoral head. The at least in sections concavely configured reception region preferably comprises an at least in sections, in particular only in sections, or fully concave inner face/articular or glide face of the artificial femoral liner. Particularly preferably, the at least in sections concavely configured reception region is defined or formed by the at least in sections concave inner face/articular or glide face and by a circumferential edge, bounding the at least in sections concave inner face/articular or glide face, of the artificial femoral liner.

The artificial femoral liner is preferably at least in sections, in particular only in sections, or fully configured in the form of a shell segment, particularly in the form of a spherical shell segment. Preferably, the artificial femoral liner comprises an at least in sections, in particular only in sections, or fully convex outer face/articular or glide face and an at least in sections, in particular only in sections, or fully concave inner face/articular or glide face, which are respectively bounded by a circumferential edge of the artificial femoral liner. Particularly preferably, the artificial femoral liner has a convex outer shape complementary to the concavely configured reception region of the artificial acetabular liner.

Alternatively, the artificial femoral liner preferably comprises an at least in sections, in particular only in sections, or fully conically or frustoconically configured reception region for receiving an artificial femoral head. The at least in sections conically or frustoconically configured reception region preferably comprises an at least in sections, in particular only in sections, or fully conical or frustoconical inner face/articular or glide face of the artificial femoral liner. Particularly preferably, the at least in sections conically or frustoconically configured reception region is defined or formed by the at least in sections conical or frustoconical inner face/articular or glide face and by a circumferential edge, bounding the at least in sections concave inner face/articular or glide face, of the artificial femoral liner. Preferably, the artificial femoral liner comprises an at least in sections, in particular only in sections, or fully conical or frustoconical outer face/articular or glide face and an at least in sections, in particular only in sections, or fully conical or frustoconical inner face/articular or glide face, which are respectively bounded by a circumferential edge of the artificial femoral liner. Particularly preferably, the artificial femoral liner has a conical or frustoconical outer shape complementary to the conically or frustoconically configured reception region of the artificial acetabular liner.

Preferably, the artificial femoral liner comprises, in particular exclusively, a plastic, preferably polyethylene, in particular ultrahigh molecular weight polyethylene, and optionally an antioxidant, in particular vitamin E.

In a further embodiment of the invention, the hip implant system furthermore comprises an artificial femoral head, in particular with or without an artificial femoral stem. Expediently, the artificial femoral head can be inserted into the artificial femoral liner. Preferably, the artificial femoral liner and the artificial femoral head (likewise) form a ball-and-socket joint in a joined or mounted state, in particular after the artificial femoral head has been inserted into the artificial femoral liner. Preferably, the artificial femoral liner comprises an insertion opening which is smaller than the outer dimension of the artificial femoral head (to be inserted). In other words, the insertion opening of the artificial femoral liner is preferably smaller than the greatest distance between two points on an outer face/glide face, in particular a convex, conical or frustoconical outer face/glide face, of the artificial femoral head (to be inserted). Preferably, the artificial femoral liner and the artificial femoral head therefore form a cotyloid joint in a joined or mounted state, in particular after the artificial femoral head has been inserted into the artificial femoral liner.

The artificial femoral head is preferably configured spherically or partially spherically. Preferably, the artificial femoral head comprises a reception region, particularly in the form of a reception recess or indentation, preferably in the form of a cylindrical or conical reception recess or indentation, for receiving a cylindrical or conical section of an artificial femoral stem. The reception region may have a circular or non-circular, in particular polygonal, for example quadrilateral, cross section.

Alternatively, the artificial femoral head may at least in sections, in particular only in sections, or fully be configured in the form of a shell segment, particularly in the form of a spherical shell segment. Preferably, the artificial femoral head comprises an at least in sections, in particular only in sections, or fully convex outer face/articular or glide face and an at least in sections, in particular only in sections, or fully concave inner face, which are respectively bounded by a circumferential edge of the artificial femoral head. Particularly preferably, the artificial femoral head has a convex outer shape complementary to the concavely configured reception region of the artificial femoral liner. Alternatively, the artificial femoral head preferably has a conical or frustoconical outer shape complementary to the conically or frustoconically configured reception region of the artificial femoral liner.

Furthermore, the femoral head may comprise a ceramic or a plastic or consist of a ceramic or a plastic.

Further features and advantages of the invention may be found from the following description of preferred exemplary embodiments of the invention, which are represented with the aid of the drawings.

DETAILED DESCRIPTION

Figure 1:
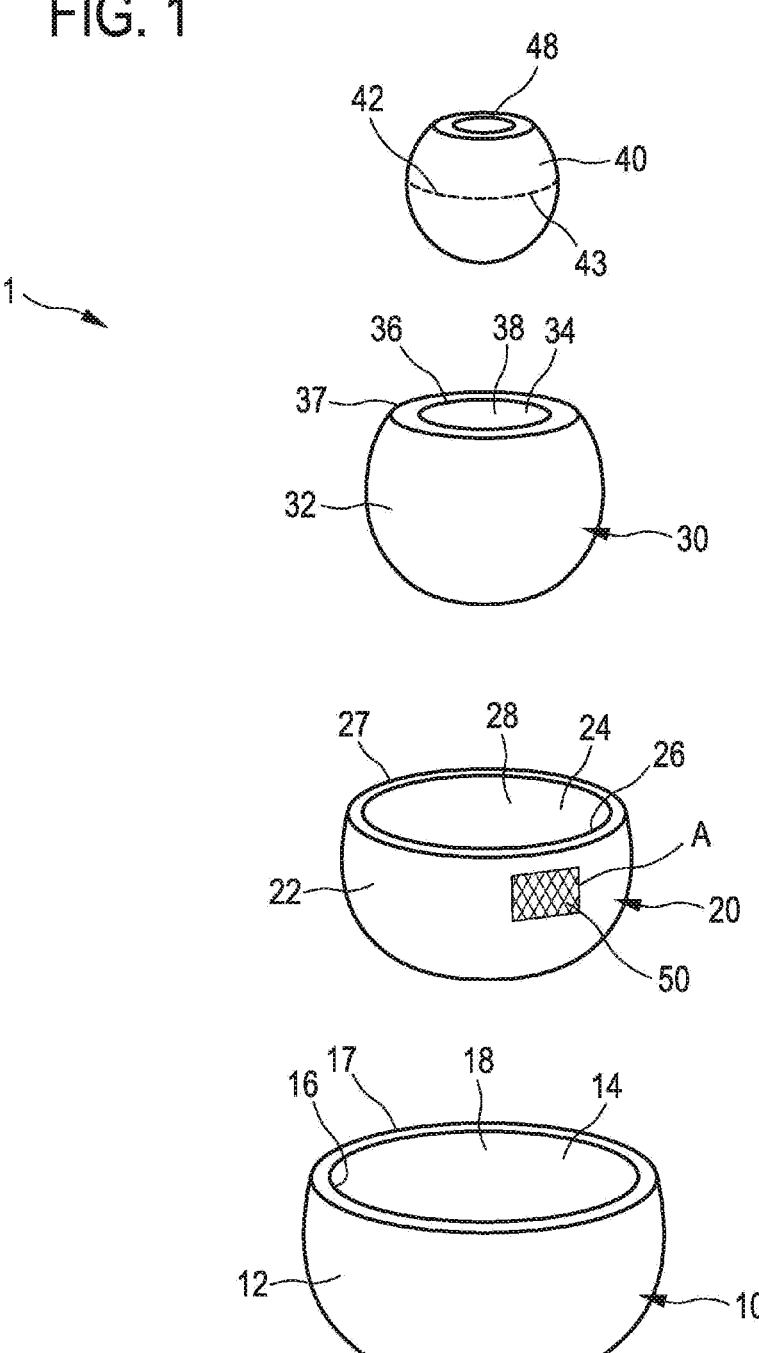
FIG. 1 shows a schematic exploded representation of an embodiment of a hip implant system according to the invention, FIG. 2 schematically shows an enlarged detail representation of a ceramic coating of a hip implant system according to the invention in a region A according to FIG. 1, and FIG. 3 schematically shows an embodiment of a hip implant system according to the invention in the mounted or implanted state.

FIG. 1 schematically shows an embodiment of a hip implant system 1 according to the present invention.

The hip implant system 1 comprises an artificial acetabular cup 10 and an artificial acetabular liner 20 which can be inserted into the artificial acetabular cup 10. The hip implant system 1 may furthermore comprise an artificial femoral liner 30 and in particular an artificial femoral head 40.

The artificial acetabular cup 10 is preferably at least in sections, in particular only in sections, or fully configured in the form of a spherical shell segment. Preferably, the artificial acetabular cup 10 comprises an at least in sections convex outer face 12 and an at least in sections concave inner face 14, which are respectively bounded by a circumferential edge 16, 17 of the artificial acetabular cup 10. In this case, the at least in sections concave inner face 14 and the circumferential edge 16 form an at least in sections concavely configured reception region 18 for the artificial acetabular liner 20.

The artificial acetabular cup 10 is preferably made from a biocompatible metal, for example titanium. In order to achieve sufficient osseointegration and in particular secondary stability, an open-pored titanium or hydroxyapatite coating may be formed on the at least in sections convexly configured outer side of the artificial acetabular cup 10.

The artificial acetabular liner 20 is likewise preferably at least in sections, in particular only in sections, or fully configured in the form of a spherical shell segment. Preferably, the artificial acetabular liner 20 comprises an at least in sections convex outer face 22 and an at least in sections concave inner or glide face 24, which are respectively bounded by a circumferential edge 26, 27 of the artificial acetabular liner 20. In this case, the at least in sections concave inner or glide face 24 and the circumferential edge 26 form an at least in sections concavely configured reception region 28 for the artificial femoral liner 30.

The at least in sections convex outer face 22 of the artificial acetabular liner 20 preferably has a surface roughness Ra of $\leq 1$ μm, preferably $\leq 0.6$ μm. In this way, optimization of the interlocking of the at least in sections convex outer face 22 with the at least in sections concave inner face 14 of the artificial acetabular cup 10 may be achieved advantageously.

The at least in sections concave inner or glide face 24 of the artificial acetabular liner 20 preferably has a surface roughness Ra of $\leq 0.5$ μm, preferably $\leq 0.05$ μm. In this way, optimized interlocking of the at least in sections concave inner or glide face 24 with an outer or glide face of the artificial femoral liner 30 may be achieved particularly advantageously.

Furthermore, the artificial acetabular liner 20 and the artificial acetabular cup 10 are clamped, preferably conically clamped, to one another in a mounted state.

The artificial acetabular liner 20 consists of an alloy containing cobalt and/or chromium, preferably a cobalt-chromium-molybdenum alloy.

The artificial acetabular liner 20 is at least in sections, in particular only in sections, or fully coated or provided with a ceramic coating 50. The ceramic coating preferably comprises chromium nitride (CrN), chromium carbonitride (CrCN), chromium zirconium nitride (CrZrN) and zirconium nitride (ZrN). In particular, the ceramic coating 50 may consist of the aforementioned ceramic materials.

Particularly preferably, the ceramic coating 50 comprises at least one chromium nitride layer (CrN layer), in particular (only) one or a plurality of chromium nitride layers, for example two or three chromium nitride layers, and/or at least one chromium carbonitride layer (CrCN layer), in particular (only) one or a plurality of chromium carbonitride layers, for example two chromium carbonitride layers, and/or at least one chromium zirconium nitride layer (CrZrN layer), in particular (only) one or a plurality of chromium zirconium nitride layers, and/or at least one zirconium nitride layer (ZrN layer), in particular (only) one or a plurality of zirconium nitride layers. The ceramic coating 50 may, in particular, consist of one or more of the aforementioned layers or of all the aforementioned layers.

Preferably, the ceramic coating 50 has a thickness of from 0.5 μm to 10 μm.

In an uncoated state, the artificial acetabular liner 20 may furthermore have, in particular, a wall thickness of from 2 mm to 3 mm.

By the ceramic coating 50, in vivo release of cobalt ions and/or chromium ions into surrounding patient tissue advantageously may be reduced or even entirely avoided. This in turn reduces the risk of postsurgical complications, particularly in the form of infections. As a result, the risk of a postsurgical reintervention may therefore be significantly reduced.

The artificial femoral liner 30 is likewise preferably at least in sections, in particular only in sections, or fully configured in the form of a spherical shell segment. Preferably, the artificial femoral liner 30 has an at least in sections convex outer or glide face 32 and an at least in sections concave inner or glide face 34, which are respectively bounded by a circumferential edge 36, 37 of the artificial femoral liner 30. In this case, the at least in sections concave inner or glide face 34 and the circumferential edge 36 form an at least in sections concavely configured reception region 38 for the artificial femoral head 40.

Preferably, the at least in sections concave inner or glide face 24 of the artificial acetabular liner 20 and the at least in sections convex outer or glide face 32 of the artificial femoral liner 30 form a ball-and-socket joint after implantation of the hip implant system 1.

The artificial femoral liner 30 consists of a plastic, preferably polyethylene, in particular ultrahigh molecular weight polyethylene, and optionally an antioxidant. The antioxidant may, for example, be vitamin E.

The artificial femoral head 40 is preferably configured spherically or partially spherically or (likewise) at least in sections in the form of a spherical shell segment. The artificial femoral head 40 comprises a reception region 48 for receiving an artificial femoral stem, in particular for receiving a preferably cylindrical or conical section of an artificial femoral stem. The reception region 48 is preferably configured as an indentation having a circular or non-circular cross section. For example, the indentation may have a rectangular cross section.

Preferably, the at least in sections concave inner or glide face 34 of the artificial femoral liner 30 and an at least in sections convex outer or glide face 42 of the artificial femoral head 40 form a so-called cotyloid joint. Such a cotyloid joint is distinguished in that the at least in sections convexly configured outer or glide face 42 of the artificial femoral head 40 is gripped beyond its equator 43 by the at least in sections concavely configured inner or glide face 34 of the artificial femoral liner 30, so that these components of the hip implant system 1 are prevented from falling out of one another.

Figure 2:
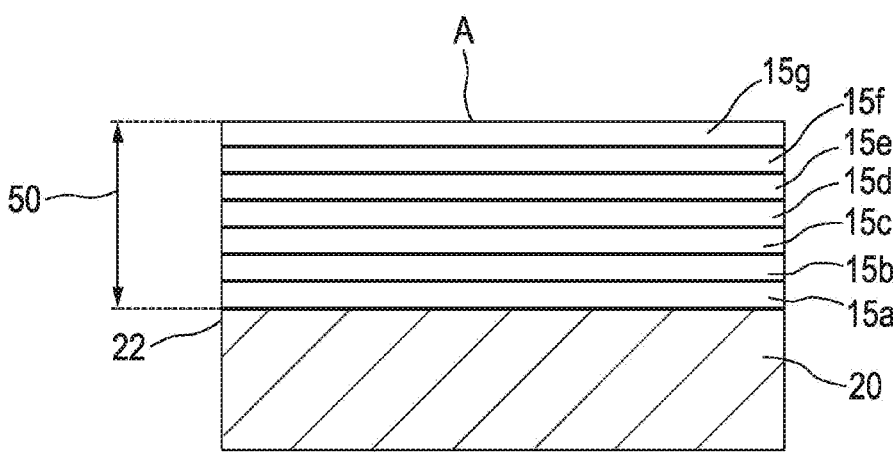

FIG. 2 schematically shows an enlarged detail representation of a preferred ceramic coating 50 according to the invention in a region A on the at least in sections convex outer face 22 of the artificial acetabular liner 20 according to FIG. 1.

The ceramic coating 50 is configured as a multilayer layer system having the following layer sequence on the at least in sections convex outer face 22 of the artificial acetabular liner 20:

The at least in sections convex outer face 22 is covered directly by a first chromium nitride layer 15a. The first chromium nitride layer 15a is covered directly by a first chromium carbonitride layer 15b. The first chromium carbonitride layer 15b is covered directly by a second chromium nitride layer 15c. The second chromium nitride layer 15c is covered directly by a second chromium carbonitride layer 15d. The second chromium carbonitride layer 15d is covered directly by a third chromium nitride layer 15e. The third chromium nitride layer 15e is covered directly by a chromium zirconium nitride layer 15f. The chromium zirconium nitride layer 15f is covered directly by a zirconium nitride layer 15g, which at the same time constitutes the cover layer of the ceramic coating 50. Alternatively, the third chromium nitride layer 15e may be covered directly by a cover layer of zirconium nitride (not represented).

Alternatively, an intermediate layer, for example made of zirconium, a zirconium alloy or a ceramic containing zirconium, may be formed between the artificial acetabular liner and the ceramic coating 50 (not represented).

Figure 3:
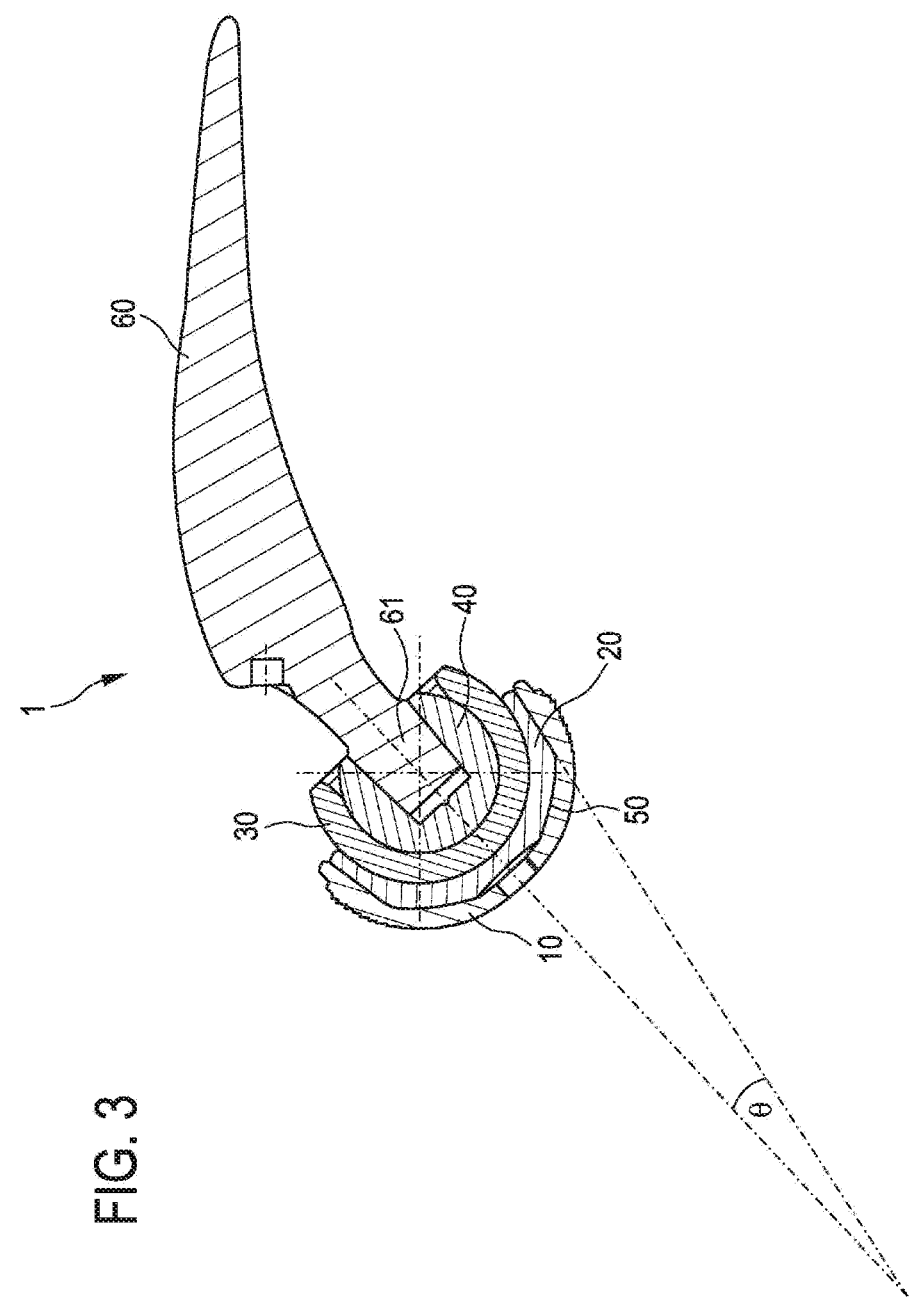

FIG. 3 shows an embodiment of a hip implant system 1 in a mounted or implanted state.

The hip implant system comprises an artificial acetabular cup 10, an artificial acetabular liner 20, an artificial femoral liner 30, an artificial femoral head 40 and an artificial femoral stem 60.

The artificial acetabular liner 20 is coated at least in sections, in particular only in sections, or fully with a ceramic coating 50. The artificial acetabular liner 20 may in particular have a cone angle θ of from 15° to 25°, in particular 16° to 21°. Advantageously, high clamping forces may therefore be produced between the artificial acetabular liner 20 and the artificial acetabular cup 10 in the joined state.

The artificial femoral stem 60 is inserted by means of a cylindrical or conical section 61 into the artificial femoral head 40.

In respect of further features and advantages of the hip implant system 1, in particular the artificial acetabular cup 10, the artificial acetabular liner 20, the artificial femoral liner 30, the artificial femoral head 40, the ceramic coating 50 and the artificial femoral stem 60, full reference is made to the descriptions relating to FIGS. 1 and 2. The features and advantages insofar as they are described there also apply correspondingly for the hip implant system 1 represented in FIG. 3.

The invention claimed is:

1. A hip implant system comprising:
an artificial acetabular cup; and
an artificial acetabular liner comprising a metal or an alloy,
wherein the artificial acetabular liner is coated at least in sections with a ceramic coating, and
wherein the ceramic coating is formed as a multilayer layer system in which a first chromium nitride layer is covered by a first chromium carbonitride layer, the first chromium carbonitride layer is covered by a second chromium nitride layer, the second chromium nitride layer is covered by a second chromium carbonitride layer, the second chromium carbonitride layer is covered by a third chromium nitride layer, the third chromium nitride layer is covered by a chromium zirconium nitride layer and the chromium zirconium nitride layer is covered by a zirconium nitride layer.

2. The hip implant system according to claim 1, wherein only an outer face of the artificial acetabular liner or only an inner face of the artificial acetabular liner is coated at least in sections with the ceramic coating.

3. The hip implant system according to claim 1, wherein the artificial acetabular liner is coated fully with the ceramic coating.

4. The hip implant system according to claim 1, wherein the ceramic coating comprises at least one non-oxide ceramic.

5. The hip implant system according to claim 1, wherein the ceramic coating is formed directly on the artificial acetabular liner.

6. The hip implant system according to claim 1, wherein the ceramic coating has a thickness of from 0.5 µm to 10 µm.

7. The hip implant system according to claim 1, wherein an inner face of the artificial acetabular liner has a surface roughness of ≤0.5 µm; and/or an outer face of the artificial acetabular liner has a surface roughness of ≤1 µm; and/or the artificial acetabular liner has a wall thickness of from 2 mm to 3 mm; and/or the artificial acetabular liner has a cone angle θ of from 15° to 25°.

8. The hip implant system according to claim 1, wherein the artificial acetabular liner and the artificial acetabular cup are connected to one another with a friction fit in a joined state.

9. The hip implant system according to claim 1, wherein the alloy comprises cobalt and/or chromium.

10. The hip implant system according to claim 1, further comprising an artificial femoral liner and/or an artificial femoral head.

11. The hip implant system according to claim 1, wherein only a convex, conical or frustoconical outer face of the artificial acetabular liner or only a concave, conical or frustoconical inner face of the artificial acetabular liner is coated at least in sections with the ceramic coating.

12. The hip implant system according to claim 4, wherein the at least one non-oxide ceramic is selected from the group consisting of chromium nitride, chromium carbonitride, chromium zirconium nitride and zirconium nitride.

13. The hip implant system according to claim 1, wherein the first chromium nitride layer is formed directly on the artificial acetabular liner.

14. The hip implant system according to claim 9, wherein the alloy containing cobalt and/or chromium is a cobalt-chromium-molybdenum alloy.

15. A hip implant system comprising:

an artificial acetabular cup; and an artificial acetabular liner comprising a metal or an alloy, wherein the artificial acetabular liner is coated at least in sections with a ceramic coating, wherein the ceramic coating comprises three chromium nitride layers, two chromium carbonitride layers, one chromium zirconium nitride layer and one zirconium nitride layer, and wherein one of the chromium nitride layers is formed directly on the artificial acetabular liner.

* * * * *